United States Patent [19]

Goldstein

[11] Patent Number: 5,043,426
[45] Date of Patent: Aug. 27, 1991

[54] PROCESS FOR MANUFACTURING ORGANIZED COLLAGEN STRUCTURES, PARTICULARLY OF HUMAN ORIGIN, AND ORGANIZED COLLAGEN STRUCTURES CORRESPONDING THERETO

[75] Inventor: Israel Goldstein, Paris, France

[73] Assignee: Diatech S. A., Nanterre, France

[21] Appl. No.: 214,346

[22] Filed: Jul. 1, 1988

[30] Foreign Application Priority Data

Jul. 1, 1987 [FR] France ............................... 87 09297

[51] Int. Cl.$^5$ ............................................. C07K 15/20
[52] U.S. Cl. ................................... 530/356; 424/423; 514/21
[58] Field of Search ......................................... 530/356

[56] References Cited

U.S. PATENT DOCUMENTS 4,242,291  12/1980  Hughes ................................... 264/1

FOREIGN PATENT DOCUMENTS 0080956  6/1983  European Pat. Off. .

OTHER PUBLICATIONS

Trommsdorf, Chem. Abst., vol. 85, 1976, 51730a.

Primary Examiner—Howard E. Schain
Assistant Examiner—Choon P. Koh
Attorney, Agent, or Firm—Armstrong, Nikaido, Marmelstein, Kubovcik & Murray

[57] ABSTRACT

The invention relates to a process for manufacturing organized collagen structures, particularly of human origin and the organized collagen structures corresponding thereto. These organized structures may be either fibres or membranes. According to the process, a specimen of animal or human tissue is ground in a saline solution after washing and aseptization, in order to solubilize the collagen contained in said specimen. There is then added to the extract thus obtained, which is composed of a minimum quantity of collagen fibrils and which is free of non-fibrillary collagen precipitate, a catalyst promoting the reconstitution of collagen fibres. Following a maturation process, the reconstituted organized structures are separated from the aqueous medium by centrifuging, and are then washed, aseptized, conditioned, lyophilized and sterilized. Among the organized structures obtained, the collagen fibers appear in the isolated state, separated from their original cellular tissue, in the form of a web (35), ready for use. They display a periodicity of transverse striations (37) comprised between 68 nm and 72 nm.

34 Claims, 5 Drawing Sheets

PROCESS FOR MANUFACTURING ORGANIZED COLLAGEN STRUCTURES, PARTICULARLY OF HUMAN ORIGIN, AND ORGANIZED COLLAGEN STRUCTURES CORRESPONDING THERETO

BACKGROUND OF THE INVENTION

1. Field of the Invention

The invention relates to a process for manufacturing organised collagen structures, in particular of human origin, and organised collagen structures corresponding thereto.

2. Brief Description of the Prior Art

It is known that collagen is the most abundant protein in mammals. It constitutes the principal fibrous element of skin, of the bones, tendons, cartilages, blood vessels and of the teeth. It is present in smaller proportions in almost all organs; it appears in the form of organised structures linked to cellular tissue, which structures are fibers or membranes.

The basic structural unit of an organised collagen structure is the tropocollagen fibril. The tropocollagen fibrils combine either to form collagen fibers which display, among other features, striations perpendicular to their axis spaced at approximately 70 nm relative to each other as well as a very high tensile strength, or to form collagen membranes.

The collagen fibers and membranes being very important constituents of the human body, attempts have been made at the in vitro reconstitution of collagen of a kind the physical and biological chacateristics of which are to closely approximate those of the collagen in vivo.

Several processes for collagen reconstitution are known to date, all starting with an animal or human tissue. One of these processes, described in 1979 by M. CHAPIL et al. in "Medical and Surgical Applications of Collagen" (International Revue of Connective Tissue Research, Vol. 6, pp. 1–55) consists in solubilizing in an acid media a part of the collagen contained in an animal tissue, namely a bovine tendon, after an enzymatic treatmen. There is obtained in this manner a collagen suspension. The latter is then reconstituted either by dialysis or by precipitation in a saline medium. The collagen structure thus obtained is an amorphous precipitate constituted by non-fibrillary denatured collagen.

This structure is in general not directly applicable for medical purposes. In fact, the collagenous material thus obtained lacks tensile strength in moist media and has little resistance against enzymatic degradation when applied to living tissues. Accordingly, this collagen must undergo special pre-treatments to remedy these drawbacks. Once these treatments have been completed, the collagen may have, among others, a gel-like or spongious form. It can then be used as haemostatic agent, as a wet surgical dressing or as a wet dressing for burns.

However, this denaturated or molecular collagen, although having undergone a treatment to reform the physical and biological characteristics approximating those of in vivo collagen, does not always satisfy requirements, in particular those of good mechanical properties in wet dressings, because it lacks the in vivo organised structure, notably the collagen fibers are not present in this artificial collagen. Moreover, the production of certain biological prostheses would require the use of collagen membranes owing to the mechanical properties of said membranes.

These considerations have led to a more detailed study of the fibrillogenesis of collagen. The fibers reconstituted from the skin of the rabbit have been found in a series of experiments described in 1969 by I. GOLDSTEIN (C.R. Academie des Sciences of Paris, vol. 268, pp. 2446–2448), but the yield of such fibers is very low, of the order of 0.5% (calculated on the weight of the original skin) when starting from an extract of animal skin.

Although these reconstituted fibers offer considerable advantages over the denaturated collagen gels, they remain nevertheless of non-human origin and are thus likely to be rejected by a human organ to which they are applied or into which they would be implanted.

BRIEF SUMMARY OF THE INVENTION

The present invention remedies the aforesaid drawbacks, by proposing a process for reconstituting organised collagen structures, especially of human origin, which process offers, due to the use of a catalyst, a fiber yield greater by a factor of about 5 than a process not using the said catalyst. The process according to the invention renders therefore feasible an industrial-scale production of such structures.

By way of human tissue as raw material there can be employed skin or placental fractions. From the skin there will be obtained collagen fibers and, according to the nature of the placental fraction employed, there will be obtained either fibers or membranes of collagen.

The reconstitution of collagen fibers from human skin is limited by the quantity of tissue which can be taken from a living being, for example in the course of an operation in cosmetic surgery. It would of course be possible to apply this process with the skin of a corpse as starting material but, independently of ethical problems, the psychological impact on the patients would be a very adverse one, particularly so in the case of an implantation of collagen in the course of cosmetic surgery.

On the other hand, human placenta is available in large quantities, notably by utilizing the organs already collected in maternity wards and conserved in the cold. In this case, however, the application of a process without catalyst of the type described by GOLDSTEIN with reference to rabbit skin (document cited above) would only produce yields of about 0.02%, which would be impractical for industrial purposes. By contrast, the application of the process according to the invention, which involves the utilization of a catalyst for the reconstitution of organised structures, more particularly fibers, allows to achieve a yield of 0.1% instead of the aforesaid 0.02%, which makes it possible to consider production on an industrial scale.

The organised structures obtained by the process according to the invention appear in the isolated state, separated from their original cellular tissue. They therefore display a structure which is analogous to the in vivo collagenous fibrillary network. Their human origin confers on them non-antigenic properties and they are accordingly very well accepted by the human body. To ensure their preservation, they can be lyophilized; their lyophilisation prior to storage imparts to them a very high resistance to biological degradation and their renewed suspension in water and/or in an isotonic buffer is practically without problems. The aqueous suspension of the fibers according to the invention, when used in man, for example by subcutaneous injection, do not provoke any of the allergies or oleomes which can be encountered when purified bovine dermal collagen (also called "zyderm") is implanted in man suspended in a physiological serum containing 0.3% of ludocaine and vegetable oil.

These reconstituted organised structures, of human origin, have many applications. They can be used in the form of fibers in cosmetic surgery operations or to confection wet dressings which promote the cicatrisation of wounds or to increase the critical value of the burn surface in very severely burnt persons. They can also be used to obtain a physiological cicatrisation of atonous wounds of vascular or neurological origin.

Moreover the ability of the organised structures to polymerise with glutaraldehyde makes it possible to visualise the fabrication of prostheses, in particular of cardiac valves. In such a case, it would be possible to select organised structures obtained from a starting material corresponding to the organ into which the prosthesis is to be implanted.

The fibers can also serve as carriers for slow-release drugs.

In the case of cosmetic surgery interventions, it is possible to take a tissue fragment from the patient, to extract the collagen therfrom and to reinject, into the same patient and at the level of the patient's wrinkles, the fibers reconstituted according to the invention.

The invention therefore has for an object a process for manufacturing organised collagen structures of animal origin, characterised in that it comprises the following sequence of process steps:

a) a fragmented animal tissue containing collagen is washed and rendered aseptic to obtain a sample free of contaminants;

b) at least a part of the collagen contained in the specimen obtained in a) is solubilised in at least one aseptic aqueous solution (SA1, SA2, SA3) of at least one diamino-derivative or a salt of an alkali or alkaline-earth metal, in particular sodium (Na), magnesium (Mg), calcium (Ca), at a pH comprised between 6.5 and 7.5 and the non-solubilised residue is separated to obtain an extract constututed by a suspension of collagen fibrils, which extract is conserved only if said suspension is free of non-fibrillary precipitate and if said suspension contains a minimum quantity of fibrile allowing for example to envisage the reconstitution of a quantity of organised structures such that this quantity be acceptable industrially and/or profitably;

c) the suspension obtained in b) is diluted with pyrogen-free water and is admixed with a catalyst for the reconstitution of the collagen fibers, said catalyst being selected from the group constituted by the monoaminosugars having a molecular weight comprised between 180 and 250 and the uronic acids or their derivatives, in particular the lactone derivatives;

d) the mixture in c) is left to mature to allow the reconstitution of the organised collagen structures;

e) the said reconstituted organised structures are separated from the aqueous medium, washed and conditioned for their subsequent use.

In process step c), advantageously galacturonic acid is employed as catalyst. Preferably, a quantity of galacturonic acid is selected such that there is established a pH comprised between 4 and 5, approximately.

In process step c), a dilution of the suspension can be selected such that the volume ratio: initial suspension/water of dilution be comprised between 1/10 and 1/20 and the catalyst is caused to act advantageously at a temperature comprised between 30° C. and 50° C., preferably at 40° C., during a time interval comprised between 30 and 90 minutes, preferably 60 minutes.

In process step d), the said mixture is advantageously left to mature at rest and at a temperature comprised between 1° C. and 10° C., preferably at approximately 4° C., during a time interval comprised between 10 hours and 100 hours.

The reconstituted organised collagen structures can be separated from the aqueous medium by centrifuging, and the organised collagen structures separated from the aqueous medium are washed preferably several times with pyrogen-free water and with ethanol.

The centrifuged liquid is advantageously recycled, adding thereto the catalyst of process step c), by leaving it to mature in a state analogous to the process step d), and by extracting the organised structures formed in a process step similar to process step e).

There is obtained, preferably, the specimen free of contaminants by fractioning the animal tissue and by washing at least once the fragments obtained with pyrogen-free water and with ethanol and said fragments can be washed with ethanol whilst stirring during a time interval comprised between 1 minute and 10 hours.

Advantageously, in process step b), at least a part of the collagene contained in the specimen is solubilised by grinding said specimen in the aqueous solution (SA1, SA2, SA3) and by shaking the homogenisate thus obtained during a time interval comprised between 10 and 30 minutes at a temperature comprised between 1° C. and 10° C., preferably at approximately 4° C., whereafter the homogenate obtained can be stirred during a time interval comprised between 12 and 36 hours at a temperature comprised between 1° C. and 10° C., preferably at approximately 4° C.

Advantageously, the residue not solubilised in process step b) is separated by screening and the residue separated by screening can be recycled in solubilization step similar to that mentioned with respect to process step b), the saline concentration of the aqueous solution (SA1, SA2, SA3) being increased from one solubilization procedure to the next until it reaches the maximum concentration utilized, the number of recycling operations being advantageously less than 10 for each saline solution employed, the extracts being subjected to process step b). In a variant of the invention, the extracts can be grouped before being subjected to process step c).

The screening element is washed with pyrogen-free water, whereafter this water is advantageously combined with the catalyst of process step c) and lastly, after a maturation stage similar to that of process step d), this second mixture is preferably added to the matured mixture of process step d).

In a first mode of execution of the process according to the invention, there is employed by way of animal tissue human skin. The organised structures then obtained are collagen fibers. Advantageously, in process step b), there is employed by way of salt for the solubilising saline solution (S1) at least one alkaline-earth metal chloride, in particular calcium chloride, at a concentration comprised between 0.5M and 2.5M.

In a second mode of execution of the process, there is employed by way of animal tissue at least one constituent of human placenta containing mainly type I and type III collagen.

Advantageously, the solubilising process step b) is carried out successively with at least two different solutions (SA1, SA2, SA3), the first (SA1) containing at least one salt of an alkali metal, in particular sodium chloride, while the second contains at least one salt of an alkaline-earth metal (SA2), in particular calcium chloride.

Advantageously, the residue obtained after the last solubilisation in the first saline (SA1) is washed at least twice with pyrogen-free water and then subjected to the action of the second saline solution (SA2) in which, by recycling the non-solubilised residues, several successive solubilisations can be achieved, all the extracts obtained by solubilisation being subjected to the catalysis of process step c). The organised structures thus obtained are collagen fibers. In a variant of the invention, the the extracts can be grouped prior to being subjected to the catalysis of process step c). In order to extract the type IV, V or VI collagen which could be additionally contained in the human placenta constituent used as starting material, the residue obtained after the last solubilisation in the second saline solution (SA2) can be washed at least once with pyrogen-free water and can be treated with a third solution (SA3) containing at least one diamino derivative in which, by recycling the non-solubilised residues, several successive solubilisations can be effected, all the extracts obtained by the solubilisation in the saline solution (SA3) being subjected to the catalysis of process step c). The organised structures then obtained are collagen membranes.

In a third mode of execution of the process according to the invention, there is selected by way of human placenta constituent one which contains mainly collagen of type IV, V and VI. The organised structures then obtained are collagen membranes.

Advantageously, the solubilisation step according to b) is carried out with at least one solution (SA3) containing at least one diamino compound. However, in order to remove from the placental constituent used as starting material the type I and III collagen which it could contain, there can be employed in the solubilisation step in b), prior to the solution (SA3), successively two different saline solutions (SA1, SA2), the first (SA1) containing at least one salt of alkali metal, in particular sodium chloride, while the second (SA2) contains at least one alkaline-earth metal salt, in particular calcium chloride.

In a fourth mode of execution of the process, there is employed by way of animal tissue a whole human placenta. The solubilisation step as in b) is then advantageously carried out successively with at least three different solutions (SA3, SA1, SA2), the first (SA3) containing at least one diamino compound in order to eliminate the major proportion of type IV, V or VI collagen contained in the placenta used as starting material, the second (SA1) containing at least one alkali metal salt and the third (SA2) containing at least one alkaline-earth metal salt.

The residue obtained after the second solubilisation in the first solution (SA3) is washed at least once with pyrogen-free water, preferably, and is then advantageously subjected to the action of the second solution (SA1) in which, by recycling the non-solubilised residues, several successive solubilisations are effected. The residue obtained after the last solubilisation in the second solution (SA1) is preferably washed at least once with pyrogen-free water and is then advantageously subjected to the action of the third solution (SA2) in which, by recycling of the non-solubilised residues, several successive solubilisations are effected, the catalysis of process step c) being preferably applied to at least all the extracts obtained by solubilisation in the solutions (SA1, SA2). The organised collagen structures then obtained are collagen fibers.

In order to extract the type IV, V or VI collagen which could possibly still be present in the residue obtained after the last solubilisation in the third solution (SA2), the said residue is preferably washed at least once with pyrogen-free water and is the advantageously subjected to the action of a fourth solution (SA3) containing at least one diamino compound in which, by recycling of the non-solubilised residues, there are effected several successive solubilisations, and all the extracts obtained by the solubilisations in the fourth solution (SA3) are subjected to the catalysis of process step c). The organised collagen structures then obtained are collagen membranes.

Advantageously, there is selected as salt of an alkaline-earth metal calcium chloride in a concentration comprised between 0.5M and 1.5M, approximately, and there can be selected as a salt of an alkali metal sodium chloride in a concentration comprised between approximately 0.5M and approximately 2M. The preferably selected diamino compound comes from the group constituted by guanidine, urea and their salts and there can be employed a concentration for the solubilising solution (SA3) comprised between approximately 2M and approximately 6M.

The organised structures then obtained can be conditioned by lyophilisation and then by sterilisation, in particular by electron beam irradiation, for example by means of an electron accelerator with a radiation dose of 2.6 Mrad.

The invention also relates to collagen fibers, characterised in that:
  they are of human origin;
  they are in an isolated state, separated from their original cellular tissue, in the form of a web and ready for use;
  they have a length comprised between 0.1 mm and 4 mm;
  they have a transverse dimension comprised between 100 nm and 500 nm;
  they have a periodicity of transverse striations comprised between 68 nm and 72 nm.

Finally, the invention relates to the organised collagen structures characterised in that they have been obtained by the aforedescribed process.

BRIEF DESCRIPTION OF THE DRAWINGS

In order to make better understood the object of the invention, there will be described in the following, by way of purely illustrative and non-limiting examples three modes of execution shown in the accompanying drawing. In the drawing.

DETAILED DESCRIPTION OF THE INVENTION

In all four modes of execution of the process, the manipulations should be effected under conditions of at least surgical sterility and at a temperature of 4° C.

Figure 1:
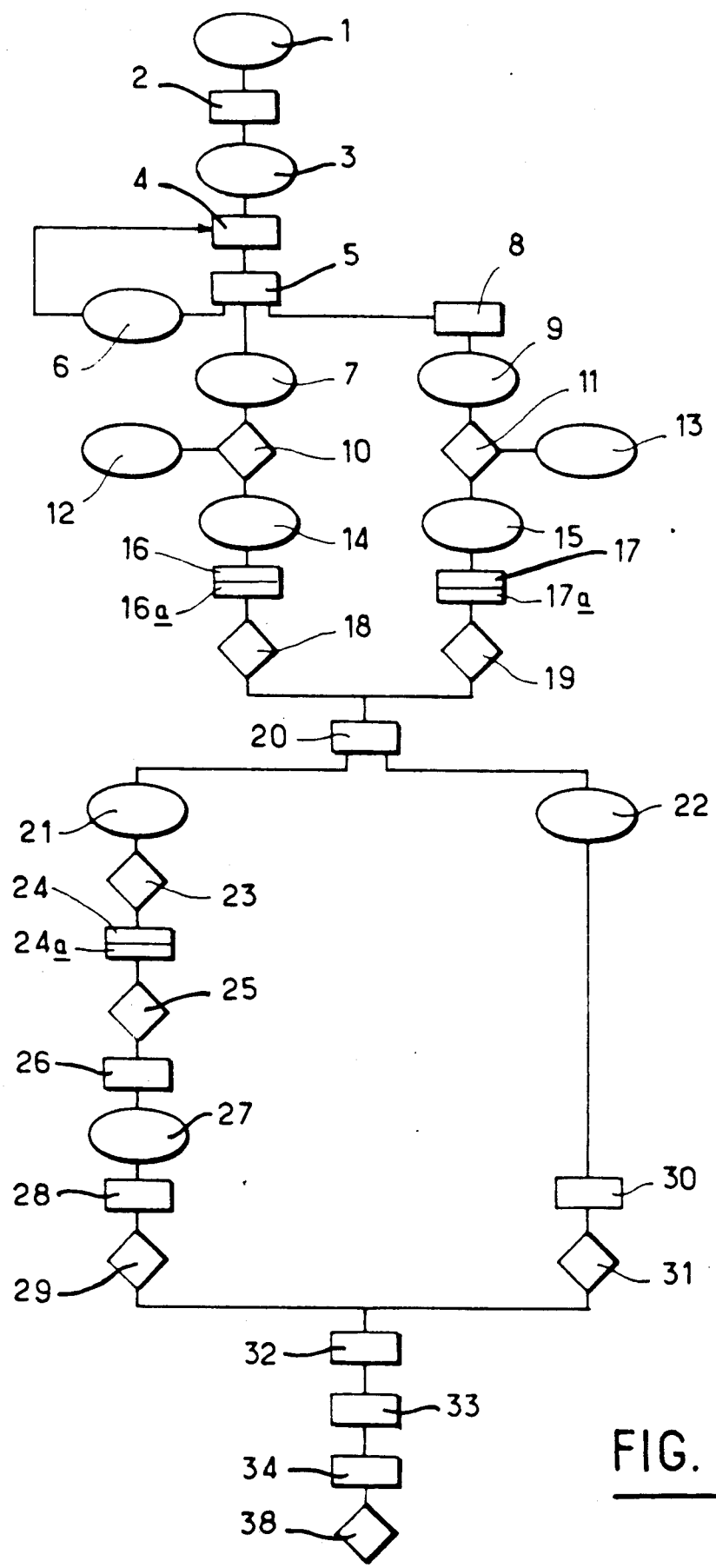
FIG. 1 shows a flowchart of a first mode of execution of the process according to the invention as applied to fragmented human skin.

In a first mode of execution the process, the flowchart of which is shown in FIG. 1, is applied to degreased human skin, obtained, for example as resections in cosmetic surgery operations. In this case, as has been previously specified, the organised structures obtained are collagen fibers.

These skin resections are frangmented and cut into fine strips so as to obtain fragments (operation 1).

These fragments are then subjected to a washing and aseptisizing operation 2. This operation consists in washing at least five times in cold, sterile, pyrogen-free distilled water the fragments obtained in operation 1, so as to free them of any blood coming from the original skin and to aseptize same by treating the with ethanol of 70% by weight. This alcoholic treatment consists in plunging the fragments into the ethanol and shaking them vigorously for 2 hours at a temperature of 4° C. This temperature contributes to avoiding a secondary infection and to prevent enzymatic activity. This use of alcohol is necessary, firstly, to disinfect the skin fragments, by killing trivial germs, and by destroying viruses, in particular capsule-coated viruses of the HIV (AIDS) type and of hepatitis B and, secondly, to deactivate all proteolytic enzymes which degrade collagen fibers. Once this ethanol-base treatment is completed, the aseptized skin fragments are again washed with cold, sterile, pyrogen-free distilled water in order to eliminate any trace of alcohol. There is thereby obtained a specimen 3 free of all contaminants.

This specimen 3 is thereafter subjected to a solubilisation operation 4 of the collagen and of the other macromolecules which it contains. Since skin contains mainly type I and type II collagen, the solubilisation of this collagen necessitates the use of an aqueous solution containing an alkaline-earth metal salt.

Therefore, an aqueous molar solution (SA1) of calcium chloride is prepared, buffered to pH 7.3 with a buffer (sodium citrate/citric acid) with a final concentration of 0.05M. The aseptized specimen 3 is then plunged into this aqueous solution (SA1) and there is selected a quantity of aqueous solution such that there is established a volume ratio (aqueous solution/specimen 3) equal to 2/1. The specimen 3 is then ground in this aqueous solution (SA1) for approximately 20 minutes with the aid of a conventional blade-type crusher at a temperature of 4° C. In order to well soak the crushed matter with the solution (SA1), the latter is then vigorously agitated for 24 hours at this temperature.

Following this solubilisation, only a part of the collagen contained in the specimen 3 has been solubilised. The mixture of crushed matter and solution is then subjected to a screening step 5, by means of two successive metal screens, both sterile and non-oxidiyable, the first having a mesh aperture of 1 mm, the other a mesh of 0.5 mm. There is then obtained, firstly, a non-solubilised residue 6 and an extract 7 constituted by a suspension of collagen fibrils.

This extract 7 is examined under the electron microscope in a control step 10. The purpose of this control is to ensure that a suspension of well-formed and well separated collagen fibrils has in fact been obtained which fibrils are free of non-fibrillary precipitates of denaturated collagen. An extract 12, containing such non-fibrillary precipitates would then be automatically rejected.

If the suspension has successfully passed this control by electron microscope, it is stored at 4° C. prior to the subsequent process step.

At the same time, the residue 6 is recycled firstly back to the solubilising step 4, in which the concentration of sodium chloride has been increased to reach a value of 1.5M. The pH-value is always kept at 7.3 and the volume ratio (solution/residue) is still 2/1. Generally speaking, in the case of specimen 3 obtained from human skin, the first two extracts are not free of non-fibrillary precipitates (and it is therefore necessary to reject them) and, furthermore, the major proportion of the collagen contained in the specimen 3 is solubilised by carrying out six recycling of the residue 6 to the solubilizing step 4. During this recycling operations, from the second to the sixth, the concentration of calcium chloride in the saline solution (SA1) is maintained at 2M. However, the number of these recycling operations depends on the degree of solubilisation of the fibers, which falls as the age of the original skin employed increases. At the end of the completed recycling operation, the non-solubilised residue 6 can be treated chemically in state-of-the art processes to produce a gel of non-fibrillary, denaturated collagen.

The extracts selected after the control step 10, generally the last five extracts, are mixed together and the resulting suspension 14 is subjected to a catalytic process step 16 and a maturing process 16a. This catalytic process step 16 consists in diluting the suspension 14 obtained with pyrogen-free water and adding thereto a catalyst promoting the reconstitution of the collagen fibers. As catalyst there is selected galacturonic acid, which is added at a rate of 0.1 mg per ml of suspension 14. There is further selected a dilution of suspension 14 such that there is obtained a pH of the said suspension of 4.5. In general, the volume ratio (initial suspension/diluent water) is comprised between 1/10 and 1/20.

Galacturonic acid has been selected because among the normal biochemical constituents of connecting tissue it is the one which provides the best yield of collagen fibers. However, monoamino sugars having a molecular weight comprised between 180 and 250 as well as uronic acids in general or their lactone derivatives could also have been selected. However, in the case where a lactons derivative is selected, the pH must be adjusted to be close to 5. The adjustment of the pH-value and the quantity of galacturonic acid added are very important because, if the quantity of galacturonic acid is increased, which amounts to lowering the pH, the precipitation of collagen is increased not in form of fibers but in the form of amorphous precipitates of denaturated collagen.

Following the addition of the galacturonic acid to the suspension, the mixture thus obtained is incubated at 40° C. for one hour. The purpose of this incubation is to facilitate the growth of collagen fibers, but it must be limited in time to avoid possible bacterial and microbial growth.

The warmed-up mixture is then left to mature at rest in process step 16a during a time interval comprised between 24 hours and 72 hours at a temperature of 4° C., during which time the reconstitution process of the collagen fibers takes place.

In parallel to the successive treatments carried out on the extracts 7, the two screens used in the screening step 6 are washed in each cycle in a process step 8 with sterile, pyrogen-free distilled water, in order to detach the collagen which has formed spontaneously on the mesh of the screens. Each wash water 9 is then recovered and subjected to a control 11 identical to control 10 of the extract 7, in order to ascertain the nature of the collagen in suspension in the wash water. A wash water containing collagen fibrils free of non-fibrillary precipitate is conserved, whilst a wash water 13 containing denaturated collagen precipitates is rejected. All the wash waters, generally the last five of them, which have been selected are mixed together and this second mixture 15 is subjected to a catalytic process step 17 and a maturation step 17a, identical to the catalytic step 16 and maturation step 16a of suspension 14.

The mixture which contains the reconstituted collagen fibers coming from the suspension 14 and the mixture containing the reconstituted collagen fibers from the mixture 15 of the screen wash water are the separately controlled under the electron microscope in control phases 18 and 19 identical to the control phases 10 and 11, and if the quality of the reconstituted fibers is satisfactory, the two mixtures are combined and subjected to a separating process step 20 to separate the collagen fibers from the aqueous medium.

This separation 20 is carried out at 4° C. by centrifuging the resulting mixture at 4,000 revs./min. for half an hour in sterile conditions. From this centrifuging phase 20 there is drawn both the reconstituted collagen fibers 22 and a centrifuged liquid 21.

The centrifuged liquid 21, which contains the collagen fibrils not yet reconstituted into fibers or collagen fibers which are incompletely formed, is subjected, after a control phase 23 identical to control phase 10, to a catalytic process step 24 and a maturation phase 24a, identical to process steps 16 and 16a. The quality of the fibers reconstituted during these process steps 24 and 24a is controlled under the electron microscope in a control phase 25 and the said fibers are separated from the aqueous medium by a centrifuging operation 26 similar to that of 20.

The collagen fibers 27 coming from the centrifuged liquid 21 and the collagen fibers 22 coming from the centrifuging phase 20 are washed at length and aseptized in washing phases 28 and 30 similar to the washing phase 2, in order to eliminate the salts and the external agents employed in the preceding treatments. The fibers, once washed and freed from all traces of alcohol, are subjected to two identical control phases 29 and 31, comprising an examination under electron microscope and immunological tests.

These tests make use of immunoenzylogical techniques to detect soluble seroproteins and to detect proteins having a structure other than that of collagen. The first of these tests is carried out with the aid of human anti-serum rabbit globulins marked with peroxydase (direct immunoperoxydase); the second test is carried out with a similar technique (indirect immunoperoxydase).

The fibers conforming to the selection criteria are then mixed and homogenised in a conditioning phase 32 in which they are stored in vials of neutral glass of 50 ml capacity.

The vials are then lyophilised in process step 33, which allows the fibers to conserve their stability and to acquire a high resistance to biological degradation, mainly in the umbilical cord, in the chorial placenta, in the walls of blood vessels, in the amniotic membrane and in the connecting tissues of the placenta. Each of the aforementioned elements contains different types of collagen. Thus, collagen of type I and III is found in the blood vessels and in the umbilical cord, collagen of type V and VI in the amniotic membrane and, lastly, collagen of type in the chorial placenta. Collagen of type I and III yields fibers, whilst the collagen of type IV, V and VI generates membranes.

Human placenta collected in the maternity wards and stored in the cold is not directly usable for the process according to the invention. It is necessary, in a first phase, to grind this placenta and to treat it with a 0.9% sodium chloride solition and 8% ethanol, then drying it and refreezing it at −20° C. There is obtained in this manner a placentary stroma to which the process according to the invention can be applied. However, given the complexity of the constitution of the placenta and the plurality of collagen types contained in this organ, the application of the process for reconstituting organised structures to the whole placental stroma is bound to fail unless special measures are taken, and would not yield either fibers or membranes but merely amorphous precipitates of collagen. One of these measures consists in extracting from this placental stroma fractions containing, for example, either primarily type I and III collagen, or primarily the type IV, V or VI collagen, depending on the nature of the structures desired to be obtained. Another measure consists in applying a particular biochemical treatment to a whole placental stroma in order to be in the presence of placental fractions containing primarily type I and type III collagen. There will then be obtained essentially collagen fibers.

Figure 2:
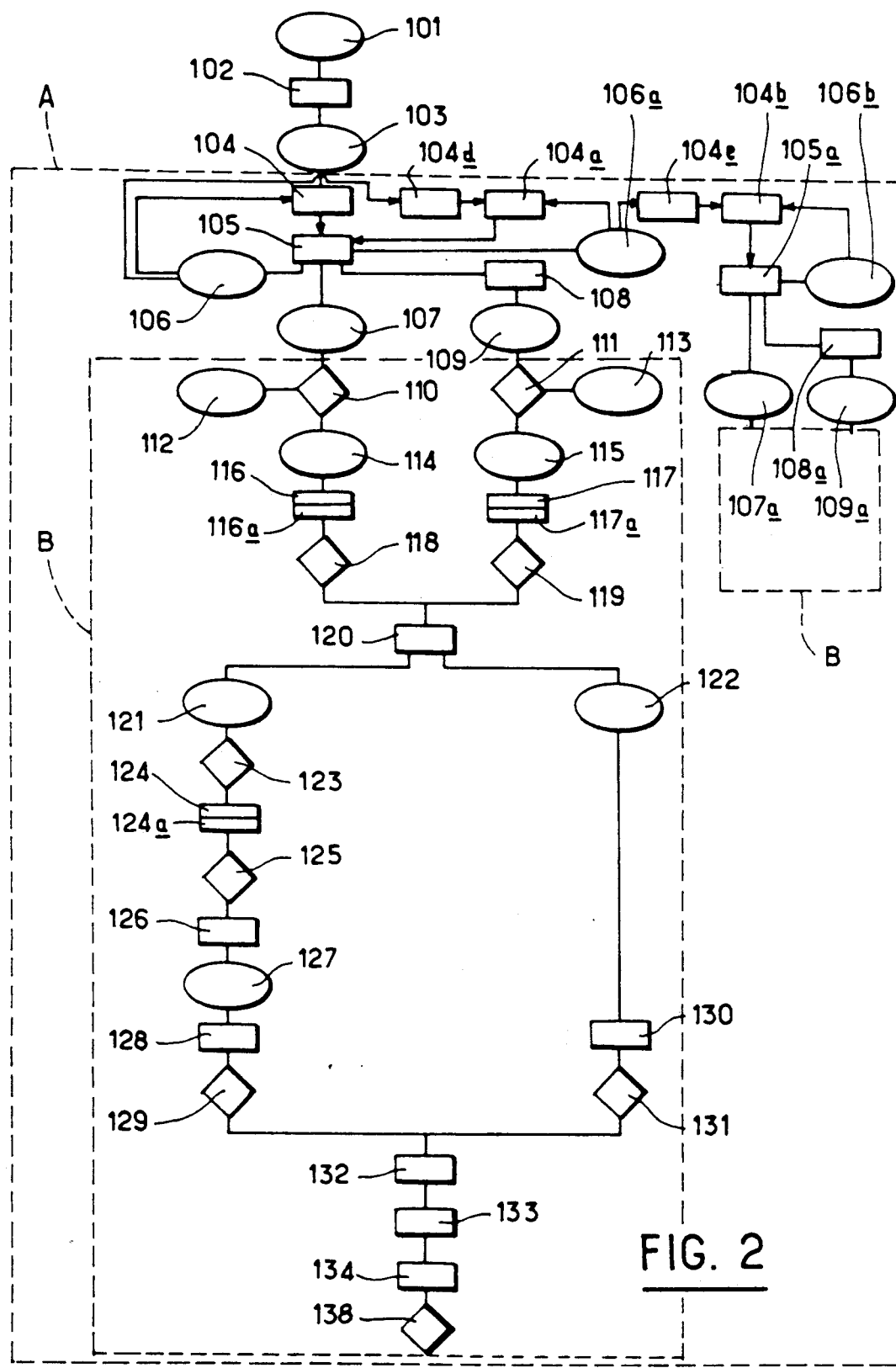
FIG. 2 is a flowchart of a second mode of execution of the process according to the invention as applied to a fraction of human placenta containing mainly collagen of type I and III.

Referring now to FIG. 2, the latter shows a flowchart of a second mode of execution of the process according to the invention, the elements of which analogous to that of the flowchart of the first mode of execution bear reference numerals greater than 100. In what follows only the differences between the two modes of execution will be described.

This second mode of execution is applicable to a fraction of the placental stroma containing mainly type I and type III collagen. The fraction 101 of the placentary stroma, after being washed and aseptized in a washing phase 102, yields a specimen 103 ready to be subjected to a solubilising phase. The type III collagen contained in specimen 103 is composed of younger and more easily solubilisable fibers than the type I collagen. For this reason, if in the solubilising process step 104 the same salt, namely calcium chloride, would be used as in the solubilising step 4 in the case of skin, there would be obtained a non-fibrillary precipitate of denaturated collagen. In the remainder of the text, the series of treatments extending from the solubilising process step 104 to the final control 138 (analogous to the final control 38) is designated by the letter A.

Accordingly, in a first phase, there is prepared in this solubilising process step 104 a first aqueous solution (SA1) containing sodium chloride at a concentration of 0.5M. This solution is buffered to pH 7.3 with the same buffer which was used in the solubilising phase 4, but the volume ratio (SA1/specimen) is of 5/1. The specimen 103 is then ground in this saline solution (SA1) in the same manner as in process step 4. Following a screening phase 105, the non-solubilised residue 106 obtained is recycled to the solubilising phase 104 by increasing from one cycle to the next the concentration of sodium chloride, the number of cycles being limited to seven. Thus, there will be used a concentration equal to 1M for the second cycle, 1.5M for the third and fourth cycle and 2M for the fifth, sixth and seventh cycles.

The residue 106, obtained after the last solubilisation in the first saline solution (SA1) washed at length with pyrogen-free water in a washing phase 104$d$ in order to eliminate this first saline solution and is then subjected to a second solubilising process step 104$a$, which utilises a second saline solution (SA2). This second solution (SA2) differs from the solution (SA1) in the nature of the salt used. It can in fact be supposed after the solubilisation step 104 that the major part of the type III collagen has been solubilised. There thus remains the type I collagen to be solubilised and there will be employed as salt for this second saline solution (SA2) calcium chloride, in a concentration rising from 0.5M in the first cycle to 1.0M for the last cycle. There are also carried out in this second solubilising phase 104 six recycling of the residue 106$a$; there is selected, for this second cycle, a calcium chloride concentration equal to 0.5M, as well as for the third and fourth cycles, and a calcium chloride concentration equal to 1M for the fifth, sixth and seventh cycles.

The solubilising phase 104$a$ can be continued by carrying out two additional recycling of the residue 106$a$ in the molar saline solution (SA2) to which a non-toxic reducing agent, namely dithiothreitrol, in a final concentration of 2 mM. The presence of dithiothreitrol in the saline solution (SA2) promotes the extraction of the fibers which could still be present in the residue 106$a$. At the end of these two successive solubilising phases 104 and 104$a$ there are obtained sixteen extracts 107 and sixteen screen washings 109.

These extracts 107 and these washings 109 are then subjected to control procedures 110 and 111, in order to check the quality of the fibril suspensions obtained and to eliminate those extracts and washings which contain collagen fibril suspension accompanied by precipitates of denaturated collagen materials. The extracts and the screen washings selected after these control phases are combined to form a first extract mixture 114 and a second washings mixture 115. In general, as in the case of skin, the first two extracts 107 and the first two screen washings 109 are rejected. The two mixtures 114 and 115 then undergo respectively a catalytic phase (116, 117) and a maturation phase (116$a$, 117$a$) similar to process steps 16, 17, and 16$a$, 17$a$, applied in the case of human skin and the subsequent treatments are identical to those employed in the first mode of execution of the process as shown in FIG. 1. In what follows, the series of treatments extending from the control phases 110 and 111 of the extracts and of the screen washings to the final control 138 is designated by the letter B.

After this series of treatments, it can be supposed that practically the quasi-totality of the type I and type III collagen fibers has been reconstituted but, since this stroma fraction came from placentary residues, it is possible that the last non-solubilised fraction 106$a$ also contains collagen of type IV, V or VI. It is therefore expedient to extract therefrom the collagen membranes.

This is why in parallel to the treatments carried out on the sixteen extracts 107 and the sixteen screen washings 109 there can be carried out on this residue 106$a$ obtained after the sixteenth recycling a series of treatments described in the following.

The last residue 106$a$ obtained is washed at length with pyrogen-free water in a washing phase 104$a$, analogous to the washing phase 104$d$, so as to eliminate the saline solution (SA2) and the dithio-threitrol, and is then recycled to a solubilising process step 104$b$, analogous to the process step 104$a$, but one in which the saline solution (SA2) is replaced by a solution (SA3). In this last-mentioned solution (SA3), the metal chloride salt has been replaced by a diamino compound. The diamino compound selected for this purpose is guanidine chlorhydrate. The solution (SA3) is likewise buffered to pH 7.3 and there is also added to it dithio-threitrol, at a final concentration of 2 mM. The volume ratio ((SA3)-solution/residue 106$a$) equals 5/1. The residue 106$a$ is washed and ground for a first time in the phase 104$b$, in the solution (SA3) in which the concentration of guanidine chlorhydrate equals 4M and, after a screening phase 106$a$ analogous to phase 105, the residue 106$b$ obtained is recycled once in this phase 104$b$, the concentration of guanidine chlorhydrate being equal to 6M. At the output of this solubilising phase 104$b$ there are obtained two extracts 107$a$ and two screen washings 109$a$ (said screens having been washed in a phase 108$a$ similar to phase 108), which extracts and washings are subjected to treatments analogous to the treatment series B for the sixteen preceding extracts 107 and 109. There are then obtained reconstituted collagen membranes 122 and 127.

Figure 3:
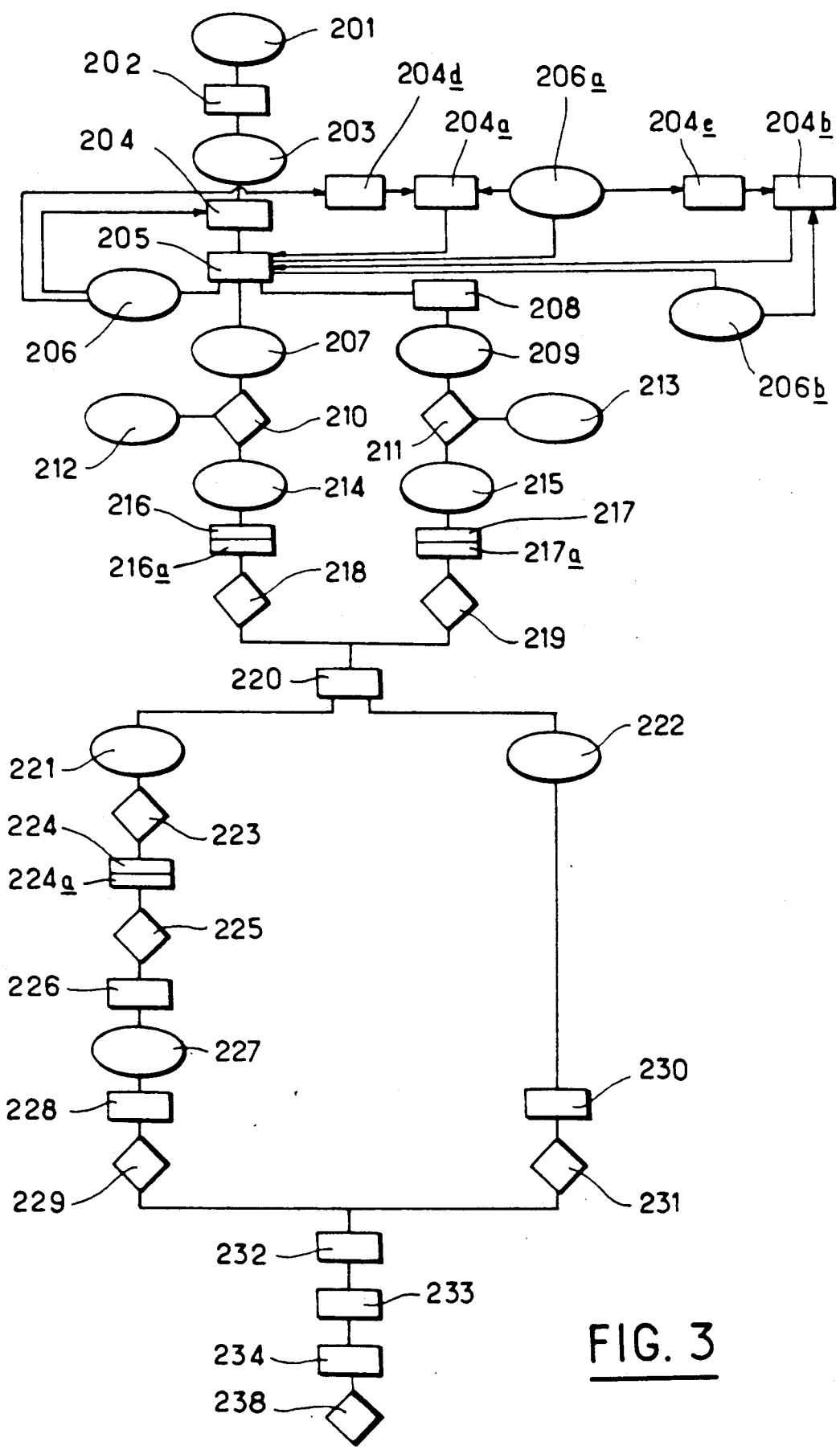
FIG. 3 is the flowchart of a third mode of execution of the process according to the invention as applied to a fraction of human placenta containing mainly collagen of type IV, V or VI.

Referring now to FIG. 3, it is seen that a flowchart of a third mode of execution of the process according to the invention is illustrated therein, of which the elements analogous to that of the flowchart of the second mode of execution have been referenced in this Figure by reference numerals greater than 100. Only the differences between the two modes of execution will be described in the following.

This third mode of execution of the process is applicable to a fraction 201 of the placentary stroma containing primarily collagen of type IV, V or VI. However, this fraction 201 may contain, for the same reasons as those explained above, small quantities of type I and III collagen. The specimen 203, obtained from this fraction 201, must therefore be "purified" by removing this type I and III collagen in order to extract therefrom, at the end of the process, solely membranes of collagen of type IV, V or VI.

For this reason, the specimen 203 will be subjected to a series of solubilising procedures 204, 204$a$ analogous to phases 104 and 104$a$, in order to extract the type I and type III collagen. As the output of these solubilising phases there is obtained sixteen extracts 207 and sixteen screen washings 209. The fourteen extracts and screen washings provided by the solubilising series in the presence of sodium chloride and calcium chloride, as well as the first solubilising in presence of calcium chloride admixed with dithio-threitrol are rejected, because they only contain fibrils of type I and type III collagen in minute quantities not allowing a reconstitution in a yield acceptable on industrial scale of collagen fibers from these fibrils.

It can be assumed that after the first solubilising in presence of calcium chloride admixed with dithiothreitrol the starting specimen 203 has been practically totally "purified" of type I and type III collagen and that it is now possible to extract the collagen of type IV, V and VI.

Accordingly, the extract 207 and the screen washing 209 deriving from the last solubilisation in presence of calcium chloride admixed with dithio-threitrol are conserved, and the last non-solubilised residue 206a is washed at length in a washing phase 204e, analogous to the phase 104e, whereafter the washed residue is subjected to a solubilising phase 204b, analogous to the phase 104b, so as to obtain at the output of this phase 204b two additional extracts 207 and two additional screen washings 209.

These three extracts 207 and screen washings 209 are then controlled and undergo the treatments indicated in the second mode of execution of the process.

Figure 4:
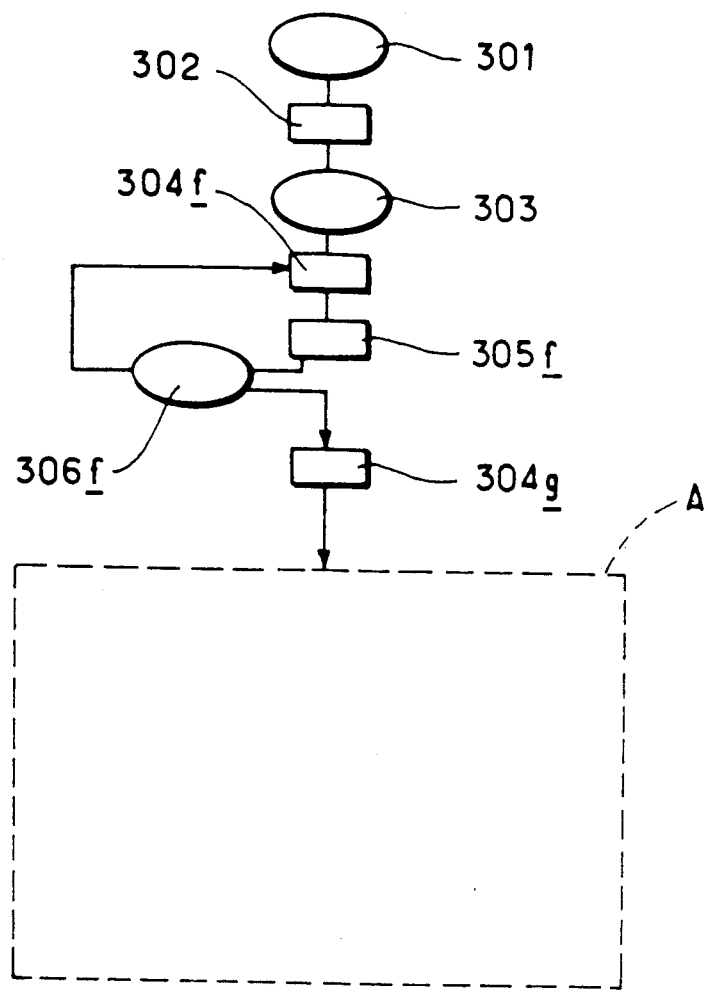
FIG. 4 is a flowchart of a fourth mode of execution of the process according to the invention as applied to a whole human placenta.

Referring now to FIG. 4, it is seen that a flowchart of a fourth mode of execution of the process of the invention is illustrated therein, of which the elements analogous to the flowchart of the second mode of execution have been referenced in this Figure by reference numerals greater than 200 relative to those employed in said second mode of execution. Only the differences between these two modes of execution will be described in the following.

This fourth mode of execution is applicable to a whole placentary stroma and makes it possible, by a biochemical treatment, to eliminate the major proportion of the type IV, V or VI collagen contained in the stroma in order to obtain a placentary stroma containing primarily type I and type III collagen. This biochemical treatment avoids all manipulation having for object the selection, prior to the application of the process, specific constituents of the placentary stroma.

The fragmented placentary stroma 301 having been washed and aseptized in a washing phase 302 therefore supplies a specimen 303 ready to undergo the biochemical treatment referred to above. This treatment consists in carrying out a solubilising process step 304f identical to the solubilising phase 104b of the second mode of execution. However, by way of diamino-compound there can be employed in the previously defined aqueous solution (SA3) urea instead of guanidine.

The specimen 303 is then ground a first time, in the phase 304f, in a solution (SA3) of the type previously defined, in which the concentration of the guanidine hydrochloride is of 4M. Following this, after a screening phase 305f analogous to the phase 105a, the residue 306f obtained is recycled once in this phase 304f, the concentration of guanidine hydrochloride being equal to 6M.

At the output of this solubilising phase 304f, it can be assumed that the major proportion of type IV, V or VI collagen has been extracted from the specimen 303 which the becomes analogous to a specimen 103 containing primarily collagen of type I and III. The extracts and screen washings obtained from phases 304f and 305f are eliminated and the residue 306f, obtained after the phase 304f, is washed at length with pyrogen-free water in a washing phase 304g, identical to the process step 104d, prior to undergoing the series of treatment A of the said second mode of execution. There will then be obtained primarily fibers of type I and type III collagen and, possibly, as indicated in the second mode of execution, collagen membranes.

Figure 5:
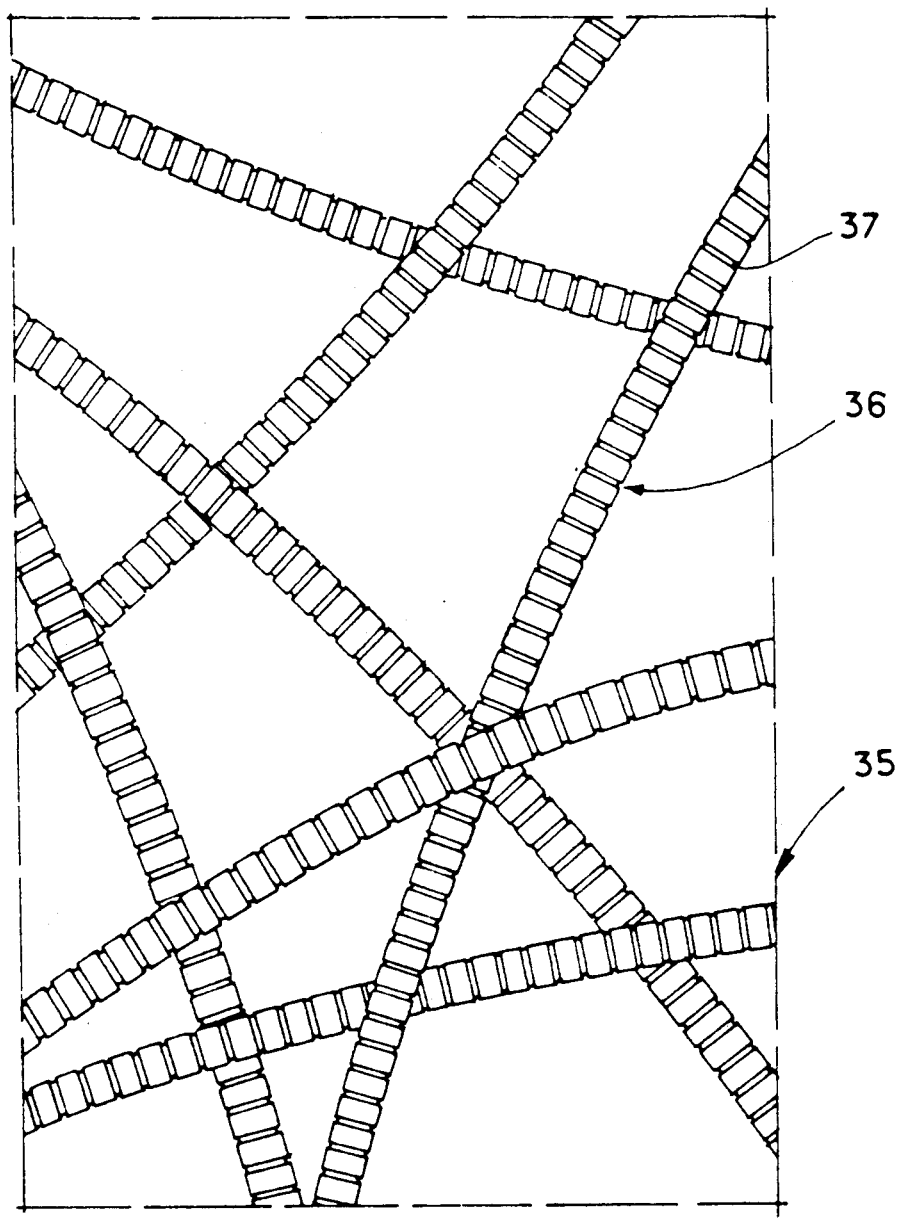
FIG. 5 shows a view of a part of the collagen fiber web obtained by the process according to the invention, as viewed through an electron microscope.

Among the organised structures obtained by the process according to the invention, the fibers are illustrated in FIG. 5. They appear in the isolated state, separated from their original cellular tissue, formed into a mesh 35. The mesh 35 is not oriented, because the orientation of the collagen fibers occurs in the organ on which they are applied or into which they are implanted, under the influence of the lines of force or of pressure exerted on the reforming connecting tissue.

The absence of toxic products during the manufacturing process, as well as the human origin of the fibers avoid all risks of toxicity and of allergic reaction.

.The fibres thus lyophilised are ready for use and can in particular be employed directly, after rehydration, on wounds or applied in a wet dressing.

It is of course understood that the modes of execution described in the foregoing have no limiting effect whatsoever and can be subjected to all desirable modifications without thereby exceeding the scope of the invention.

I claim:

1. A process for preparing organised structures of collagen of animal origin comprising the following sequence of steps:
    a) collagen-containing fragmented animal tissue is washed and sterilized to obtain a specimen free of all contaminants;
    b) at least a portion of the collagen obtained according to a) is solubilized in an aseptic aqueous solution of at least one compound selected from the group consisting of diamino compounds, alkali metal salts and alkaline-earth metal salts at a pH between 6.5 and 7.5, any non-solubilized residue is separated and a suspension of collagen fibrils, free of non-fibrillary residue is obtained;
    c) the suspension obtained according to b) is diluted with pyrogen-free water and to it is added at least one catalyst consisting of monoamino sugars having a molecular weight between 180 and 240, uronic acids and uronic acid derivatives;
    d) the mixture obtained according to c) is allowed to stand for a time sufficient for the reconstitution of the organized collagen structures;
    e) said reconstituted organized collagen structures are separated from the aqueous medium, washed and conditioned.

2. A process according to claim 1, wherein said uronic acid derivatives are lactones.

3. A process according to claim 2, wherein said uronic acid derivative is galacturonic acid.

4. A process according to claim 3, wherein said there is selected a quantity of galacturonic acid such that a pH between approximately 4 and approximately 5 is obtained.

5. A process according to claim 1, characterised in that in process step c) of claim 1 there is selected a dilution of the suspension such that the volume ratio: initial suspension/water of dilution is between 1/10 and 1/20.

6. A process according to claim 5, characterised in that in process step c) of claim 1 the catalyst is caused to act at a temperature between 30° C. and 50° C. during a time interval between 30 and 90 minutes.

7. A process according to claim 1, characterised in that in process step d) of claim 1 the said mixture is allowed to stand at rest at a temperature between 1° C. and 10° C. during a time interval between 10 hours and 100 hours.

8. A process according to claim 1, characterised in that the reconstituted organized collagen structures are separated from the aqueous medium by centrifugation.

9. A process according to claim 8, characterised in that the organised collagen structures (22, 27; 122, 127; 222, 227) separated from the aqueous medium are washed several times with pyrogen-free water and ethanol.

10. A process according to claim 8 wherein the centrifuged liquid is recycled by adding thereto the catalyst of process step c) of claim 1, allowing it to stand for a time sufficient to reconstitute organized collagen structures; and by extracting the organized collagen structures, washing and conditioning.

11. A process according to claim 1, wherein a contaminant-free specimen is obtained by fractionating the animal tissue and by washing the fragments so obtained at least once with pyrogen-free water and ethanol.

12. A process according to claim 1, wherein in process step b, at least a part of the collagen contained in the specimen is solubilized by crushing said specimen in an aqueous solution and stirring the crushed material thus obtained.

13. A process according claim 1, wherein said non-solubilized residue is separated by screening.

14. A process according to claim 13, wherein a recycling of the residue separated by screening in a slobilising process step analogous to process step b) of claim 1, the saline concentration of the aqueous solution being increased from one solubilising step to the next, the number of recycling operations being less than 10 for each saline solution employed.

15. A process according to claim 14, wherein the screening element is washed with pyrogen-free water, that this washing is admixed with the catalyst of process step c) of claim 1 and finally, after a maturation phase analogous to that of process step d) of claim 1, this second mixture is added to the matured mixture of process step d) of claim 1.

16. A process according to claim 1, wherein the animal tissue source of collagen is human skin.

17. A process according to said claim 12, wherein said aqueous solution is a salt comprising at least one chloride of an alkaline-earth metal at a concentration between 0.5M and 2.5M.

18. A process according to claim 1 wherein the animal tissue source of collagen is at least one constituent of human placenta.

19. A process according to claim 18, wherein said constituent of human is a constituent containing primarily type I and type III collagen.

20. A process according to claim 19, wherein the solubilising step is carried out according to b) in claim 1 successively with at least two different solutions, the first of said solutions containing at least one alkali metal salt while the second contains at least one alkaline-earth metal salt.

21. A process according to claim 20, in which the organized structures are collagen fibers; and wherein the residue obtained after the last solubilization in the first saline solution is washed at least once with pyrogen-free water and is then subjected to the second saline solution in which, by recycling the non-solubilized residues (106a), a plurality of successive solubilisations are performed, all of which are subjected to a catalytic process step c).

22. A process according to claim 21, in which the organised structures are collagen membranes further comprising subjecting the residue to a third solution containing at least one diamino compound and recycling of the non-solubilized residues to effect several successive solubilisations, all of which are subjected to a catalytic process according to step c).

23. A process according to claim 18, wherein said collagen membranes obtained from human placenta is selected which contains primarily type IV, V or VI collagen.

24. A process according to claim 23, wherein the solubilising process step (204b) according to b) of claim 1 is carried out with at least one solution containing a diamino compound.

25. A process according to claim 24, wherein the solubilizing process step according to step b) of claim 1 employs, prior to the application of the saline solution (SA3), successively two different saline solution, the first (SA1) containing at least one salt of an alkali metal, and a second (SA2) containing at least one salt of an alkaline-earth metal.

26. A process according to claim 18, wherein said animal tissue utilized is a whole human placenta (301).

27. A process according to claim 26, wherein the solubilization process according to step b) of claim 1 is carried out using at least three different solutions (SA3, SA1, SA2) in succession, the first (SA3) containing a least one deamino compound, the second (SA1) containing at least one salt of an alkali metal and the third (SA2) containing at least one salt of an alkaline-earth metal.

28. A process according to a claim 27, in which the organised collagen structures are collagen fibres, wherein the residue obtained after the last solubilisation in the first solution (SA3) is washed at least once with pyrogen-free water and is then subjected to the second solution (SA1) in which, by recycling the non-solubilised residues, there are carried out several solubilizing procedures in succession, and that the residue obtained after the last solubilisation in the second solution (SA1) is washed at least once with pyrogen-free water and is the subjected to the third solution (SA2) in which, by recycling the non-solubilised residues, there are effected several solubilising procedures in succession, the catalysis of process step c) of claim 1 being applied at least to all the extracts obtained by solubilisation in the solutions (SA1, SA2).

29. A process according to claim 28, wherein the residue obtained in the last solubilisation in the third solution (SA2) is washed at least once with pyrogen-free water and is then subjected to a fourth solution (SA3) containing at least one diamino compound, in which, by recycling the non-solubilised residues, several solubilising procedures are carried out in succession, all the extracts obtained by the solubilising procedures in the fourth solution (SA3) being subjected to catalysis in process step c) of claim 1.

30. A process according to claim 17, wherein said salt of alkaline-earth metal is calcium chloride, in a concentration between approximately 0.5M and approximately 1.5M.

31. A process according to claim 20, wherein said salt of alkali metal is sodium chloride, in a concentration comprised between approximately 0.5M and approximately 2M.

32. A process according to claim 22, wherein said diamino compound is selected from the group formed by guanidine, urea and their salts and that there is employed a concentration of said compounds in the solubilising solution (SA3) comprised between approximately 2M and approximately 6M.

33. A process according to claim 1 wherein the organised structures obtained are conditioned by lyophilisation and sterilization.

34. A process according to claim 33, wherein the lyophilised organised structures are sterilised by electron irradiation.

* * * * *